United States Patent [19]
Shaw

[11] Patent Number: 5,908,774
[45] Date of Patent: Jun. 1, 1999

[54] REMEDIATION OF PESTICIDE-CONTAMINATED SOIL

[76] Inventor: Edward A. Shaw, P.O. Box 7487, Athens, Ga. 30604

[21] Appl. No.: 08/426,971

[22] Filed: Apr. 24, 1995

[51] Int. Cl.$^6$ .............................. A01N 25/00; B09B 3/00; C02F 3/00; C12N 1/00
[52] U.S. Cl. ....................... 435/262.5; 435/170; 424/405; 424/406; 210/600; 210/601
[58] Field of Search .................................... 424/405, 406; 435/170, 822, 262.5; 210/600, 601

[56] References Cited

U.S. PATENT DOCUMENTS

| | | | |
|---|---|---|---|
| 4,511,657 | 4/1985 | Colaruotolo et al. | 435/253 |
| 4,664,805 | 5/1987 | Focht | 210/611 |
| 5,037,551 | 8/1991 | Barkley et al. | 210/603 |
| 5,100,455 | 3/1992 | Pinckard et al. | 71/9 |
| 5,174,893 | 12/1992 | Halpern et al. | 208/262.5 |
| 5,209,604 | 5/1993 | Chou | 405/128 |
| 5,227,136 | 7/1993 | Hanify et al. | 422/225 |
| 5,342,779 | 8/1994 | Matsumura et al. | 435/262.5 |

OTHER PUBLICATIONS

Whittenbury R and Dalton H. *The Prokaryotes: A Handbook on Habitats, Isolation and Identification of Bacteria;* Starr, MP et al. ed. 1981; 2:894–902.

Stirling DI, Colby J and Dalton H. A Comparison of the Substrate and Electron–Donor Specificities of the Methane Mono–oxgenases from Three Strains of Methane–Oxidizing Bacteria. *Biochem. J.* 1979; 177:361–364.

Saleh MA, Capillary Gas Chromatography–Electron Impact and Chemical Ionization Mass Spectrometry of Toxaphene. *Amer Chem Soc* 1983; 31:748–751.

Pepper IL and Watson JE. Treatment of Pesticide–Containing Soil. *Natl Workshop on Pesticide Waste Disposal* 1986; 28–30.

Oldenhuis R, Vink R, Janssen DB and Witholt B. Degradation of Chlorinated Aliphatic Hydrocarbons by *Methylosinus trichosporium* OB3b Expressing Soluble Methane Monooxygenase. Appl and Environ Microbio 1989; 55: 2819–2826.

Roberts PV, Hopkins GD, Mackay DM and Semprini L. A Field Evaluation of In–Situ Biodegradation of Chlorianted Ethenes: Part 1, Methodology and Field Site Characterization. *Ground Water* 1990; 28:591–604.

Roberts PV, Hopkins GD. Mackay DM and Semprini L. A Field Evaluation of In–Situ Biodegradation of Chlorianted Ethenes: Part 2, Methodology and Field Site Characterization. *Ground Water* 1991; 28:715–727.

Lanzarone NA and McCarty PL. Column Studies on Methanotrophic Degradion of Trichloroethene and 1,2–Dichloroethane. *Ground Water* 1990; 28:910–919.

Saleh MA. Toxaphene: Chemistry, Biochemistry, Toxicity and Environmental Fate. *Reviews of Environ Contamination and Toxicology* 1991; 118:1–85.

The Laboratory Testing of the Processes at Brigham Young University, Dec., 1992 to May, 1993.

The Field Testing of the Processes at the Nuodex Facility in New Jersey, Aug., 1994 to Dec., 1994.

The Report entitled "Biotreatability Study of Toxaphane Contaminated Soils from the Tenneco Chemical, Inc., Fords, New Jersey Facility," submitted to the New Jersey Department of Environmental Protection in May, 1993.

*Primary Examiner*—David M. Naff
*Assistant Examiner*—Deborah K. Ware
*Attorney, Agent, or Firm*—Arnold White & Durkee

[57] ABSTRACT

The present invention provides a method of remediating soil contaminated with organochlorine pesticides by introducing methanotrophic bacteria to the soil if methanotrophic bacteria are not present in the soil, and introducing methane and air to the methanotrophic bacteria-containing soil to effect remediation of the soil. An alternative method involves remediation of soil containing the organochlorine pesticide toxaphene using denitrifying bacteria and nitrate.

6 Claims, 16 Drawing Sheets

REMEDIATION OF PESTICIDE-CONTAMINATED SOIL

FIELD OF THE INVENTION

The present invention is an improved method for the bioremediation of soil contaminated with organochlorine pesticides.

BACKGROUND OF THE INVENTION

Organochlorine pesticides have been used heavily in the U.S. to combat a variety of insect pests. Pesticides have contaminated soils throughout chemical production facilities and from the disposal of container and spray equipment rinsewaters. The United States Environmental Protection Agency has banned most organochlorine pesticides, but not before millions of tons of the pesticides had been used in various applications across the United States. Most organochlorine pesticides are acutely toxic and mutagenic and carcinogenic under certain conditions. They have been found to be accumulated by animals and plants and are persistent in the environment under normal conditions. For example, the half-life of the organochlorine pesticide toxaphene has been estimated at 11–20 years.

Thus, organochlorine pesticides represent a serious threat to the environment and there is clearly a need for innovative technologies for the in-situ remediation of organochlorine pesticide-contaminated soils.

Excavation and incineration are remedial strategies which have been used because of the complete destruction of the contaminant and liability in a short period of time. However, they are costly and cause secondary pollution. In-situ and ex-situ chemical treatments involving oxidants, reductants, and alkalis have also been used with varying degrees of success at sites contaminated with organochlorine pesticides.

It is an object of the invention to provide a method of remediating soil contaminated with organochlorine pesticides. It is a further object of the invention to provide a method of remediating the contaminated soil which is more cost effective than the existing methods.

SUMMARY OF THE INVENTION

Figure 1:
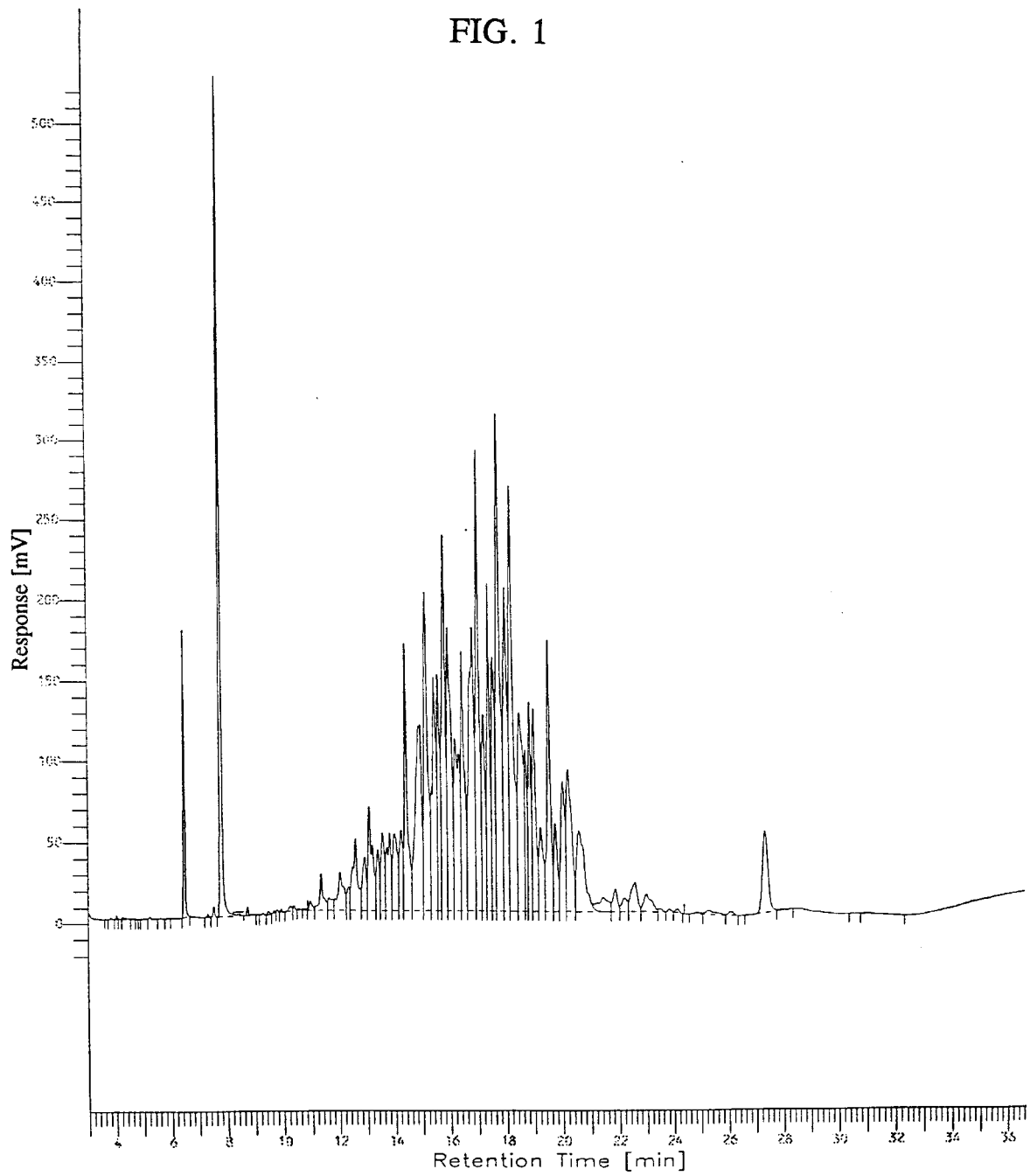
FIG. 1 is a gas chromatogram of toxaphene.

The objects of the invention are provided by a method of remediating soil contaminated with organochlorine pesticides. The method comprises the steps of (a) testing the soil for the presence of methanotrophic bacteria; (b) introducing methanotrophic bacteria to the soil if methanotrophic bacteria are not present in the soil; and (c) introducing methane and air to the methanotrophic bacteria-containing soil to effect remediation of the soil. Methane is present in the methane/air mixture at a concentration of from about 1% to about 8%, preferably about 2% to about 5%.

An alternative method comprises a method for remediating soil containing the organochlorine pesticide, toxaphene. The method comprises the steps of testing the soil for the presence of denitrifying bacteria; (b) introducing denitrifying bacteria to the soil if denitrifying bacteria are not present in the soil; and (c) introducing nitrate ($NO_3^-$) to the denitrifying bacteria-containing soil to effect remediation of the soil. Examples of nitrates are potassium nitrate, ammonium nitrate, sodium nitrate, and fertilizer mix containing nitrate salts.

Examples of organochlorine pesticides are toxaphene, dieldrin, lindane, aldrin, chlordane, endrin, endrin aldehyde, heptachlor, heptachlor epoxide, and alpha-BHC, beta-BHC, gamma-BHC, delta-BHC, 4,4'-DDD, 4,4'-DDE, 4,4'-DDT, endosulfan I, endosulfan II, endosulfan sulfate.

DETAILED DESCRIPTION OF THE INVENTION

It has been discovered that soils contaminated with organochlorine pesticides may be remediated by methanotrophic or denitrifying bacteria. The present invention is a method of remediating soil contaminated with organochlorine pesticides. The goal is to biotransform the organochloro pesticides to compounds which are more favorable to aerobic microbial metabolism or degradation, i.e., only oxygen (not methane) would be needed to further degrade the compounds ultimately to carbon dioxide and water.

Remediation Using Methanotrophic Bacteria

Remediation of soil contaminated with organochlorine pesticides using methanotrophic bacteria is carried out by a method comprising the steps of (a) testing the soil for the presence of methanotrophic bacteria, (b) introducing methanotrophic bacteria to the soil if methanotrophic bacteria are not present in the soil, and (c) introducing methane and air to the methanotrophic bacteria-containing soil to effect remediation of the soil. Methane is present in the methane/air mixture at a concentration of from about 1% to about 8%, preferably about 2% to about 5%.

Applicants conjecture that remediation of soil contaminated with organochlorine pesticides is carried out by the production by methanotrophic bacteria of the enzyme methane monooxygenase in the presence of methane. Methantrophic bacteria under most conditions, depends solely upon methane ($CH_4$) as a carbon source (electron donor) and molecular oxygen ($O_2$) as the respiratory compound (electron acceptor). The enzyme methane monooxygenase (MMO) makes methane available as an electron donor. The methane monooxygenase enzyme occurs in two forms, a soluble form and an insoluble form. The soluble form has been demonstrated to have a low substrate specificity (Stirling et al., *Biochem. J.*, 177, 361–364 (1979). That is, the enzyme will react with (cometabolize) a wide range of recalcitrant organic compounds generally unavailable as a primary carbon/energy source to microbes (Stirling et al., 1979). The soluble enzyme becomes active under conditions which are copper or methane stressed (limited). Though not as prevalent, there are facultative methanotrophs which use other electron donors in addition to methane. This process is aerobic and requires free molecular oxygen as the respiratory compound (electron acceptor).

Methane co-metabolism (usually soluble enzyme-based) has been shown to effectively dechlorinate recalcitrant compounds such as trichloroethylene, dichloroethylene, and vinyl chloride (Oldenhuis et al., *Applied and Environmental Microbiology*, pp. 2819–2826 (1989); Lanzarone et al., *Ground Water*, Vol. 28, No. 6, (1990); Roberts et al., *Ground*

*Water*, Vol. 28, No. 4, (1990); Semprini et al., *Ground Water*, Vol. 28, No. 5, pp. 715–727 (1990).

Remediation Using Denitrifying Bacteria

Remediation of soil contaminated with the organochlorine pesticide toxaphene may be accomplished using denitrifying bacteria in place of methanotrophic bacteria and introducing nitrate in place of methane and air.

The nitrate is applied to the soil either by laying the solid nitrate onto the soil and subsequently adding water to carry it down into the soil, or by preparing an aqueous solution of the nitrate and applying the solution to the soil. The effective concentration of nitrate in water may range from about 0.1% to about 10%, preferably from about 0.1 to about 5%, most preferably from about 0.5% to about 1%. Examples of nitrates which may be used are potassium nitrate, ammonium nitrate, sodium nitrate, and fertilizer mix containing nitrate salts.

Remediation of soil using methanotrophic bacteria is expected to work in any soil which contains both organochlorine pesticides and methanotrophic bacteria. Examples of organochlorine pesticides are toxaphene, dieldrin, lindane, aldrin, chlordane, endrin, endrin aldehyde, heptachlor, heptachlor epoxide, and alpha-BHC, beta-BHC, gamma-BHC, delta-BHC, 4,4'-DDD, 4,4'-DDE, 4,4'-DDT, endosulfan I, endosulfan II, endosulfan sulfate. Remediation of soil using denitrifying bacteria is expected to work in any soil which contains both denitrifying bacteria and toxaphene.

A novel method of practicing the invention comprises driving pipes into the soil to sparge a methane/air mixture into the soil to the desired depth. Previous methods used required first drilling holes into the soil before gases could be pumped into it.

EXAMPLE 1

Determination of Soil Bacterial Content. Toxaphene, a particularly troublesome organochlorine pesticide, is a complex, but reproducible, mixture of chlorinated camphenes sold under names such as Motox, Penphene, Phenacide, Phenatox, Strobane-T, and Toxakil. Toxaphene contains at least 177 $C_{10}$ polychloro derivatives of camphene having the approximate overall empirical formula of $C_{10}H_8Cl_{10}$. It is produced by the chlorination of camphene to 67–69 wt. % chlorine and made up of compounds of $C_{10}H_8Cl_{10}$, $C_{10}H_{18-n}Cl_n$ (mostly polychlorobornanes), and $C_{10}H_{16-n}Cl_n$ (polychlorobornenes and/or polychlorotricyclenes) with n=6 to 9 (*The Merck Index*, 11th ed. (1989)).

Soil in an area which was used primarily for the production and storage of the organochlorine pesticide, Strobane T-90 (toxaphene), was tested for microbial content. Soil samples were obtained from four locations (A, B, C, and D) at the site where elevated levels of toxaphene contamination had been found during site characterization activities. Extensive aromatic hydrocarbons were released throughout area A and toxaphene concentrations were detected in area A soils at concentrations of 120 mg/kg to 440 mg/kg. Areas B and C have a similar lithology (medium sand) and toxaphene concentrations of 33,000 mg/kg and 41,000 mg/kg, respectively. Soil D was collected from a thin clay layer with a toxaphene concentration of approximately 166,000 mg/kg. Both methanotrophic bacteria and denitrifying bacteria were identified in soils B, C, and D.

EXAMPLE 2

Degradation of Toxaphene by Denitrification. A 20 foot by 20 foot test plot located within the area tested in Example 1 was initially flooded with 3 to 9 inches of a 10% potassium nitrate solution. The plot was bermed with sand bags and gravel to prevent the nitrate solution from migrating out of the immediate study area.

Four ground-water monitoring points (DENMP-1 through DENMP-4) were installed in the test plot and one recovery well (DEN-MW) was installed immediately downgradient of the study area. The monitoring points were constructed of 1 inch (I.D.) PVC to a depth of approximately three feet, with a six inch section of screen (0.010 inch) and four feet of solid riser. The recovery well was constructed of four inch (I.D.) PVC to an approximate depth of twelve feet, with ten feet of screen (0.010 inch) and 5 feet of solid riser.

Ground-water samples were collected periodically from the recovery well and from the ground-water monitoring points. The samples were analyzed for dissolved chloride ($Cl^-$) and nitrate ($NO_3^-$) using EPA method 300.0. Ground-water samples were also tested in the field for $NO_3^-$ concentrations with an RQflex hand-held meter (manufactured by Merck) and Reflectoquant® strips specific for $NO_3^-$ (sensitivity range of 3 to 90 mg/L). Whenever $NO_3^-$ levels were detected in the recovery well at concentrations above 5 mg/L, the water was pumped through two activated carbon canisters and into a 1,000 gallon polyethylene holding tank. The groundwater was then recirculated through the denitrification test plot until $NO_3^-$ concentrations reached appropriate levels.

A ground-water sample was collected from the recovery well on day 81, and analyzed for toxaphene using EPA method 608. At the end of the field pilot study (day 144), another ground-water sample was collected from the recovery well. The sample was split three ways and analyzed for: (1) toxaphene using EPA method 8080, (2) toxaphene by-products using EPA 8270, and (3) apparent toxaphene using a modified EPA method 8080. The modified 8080 method involved a florisil column cleanup procedure intended to remove by-products that might interfere with the toxaphene chromatogram. (FIG. 1).

Initial time ($T_o$) soil samples were collected with a decontaminated, stainless steel hand auger on day 1. The sample locations were distributed throughout the test plot at two different depths for each location: A (6"–12") and B (18"–24"). The locations were designated L1 through L6.

Figure 2:
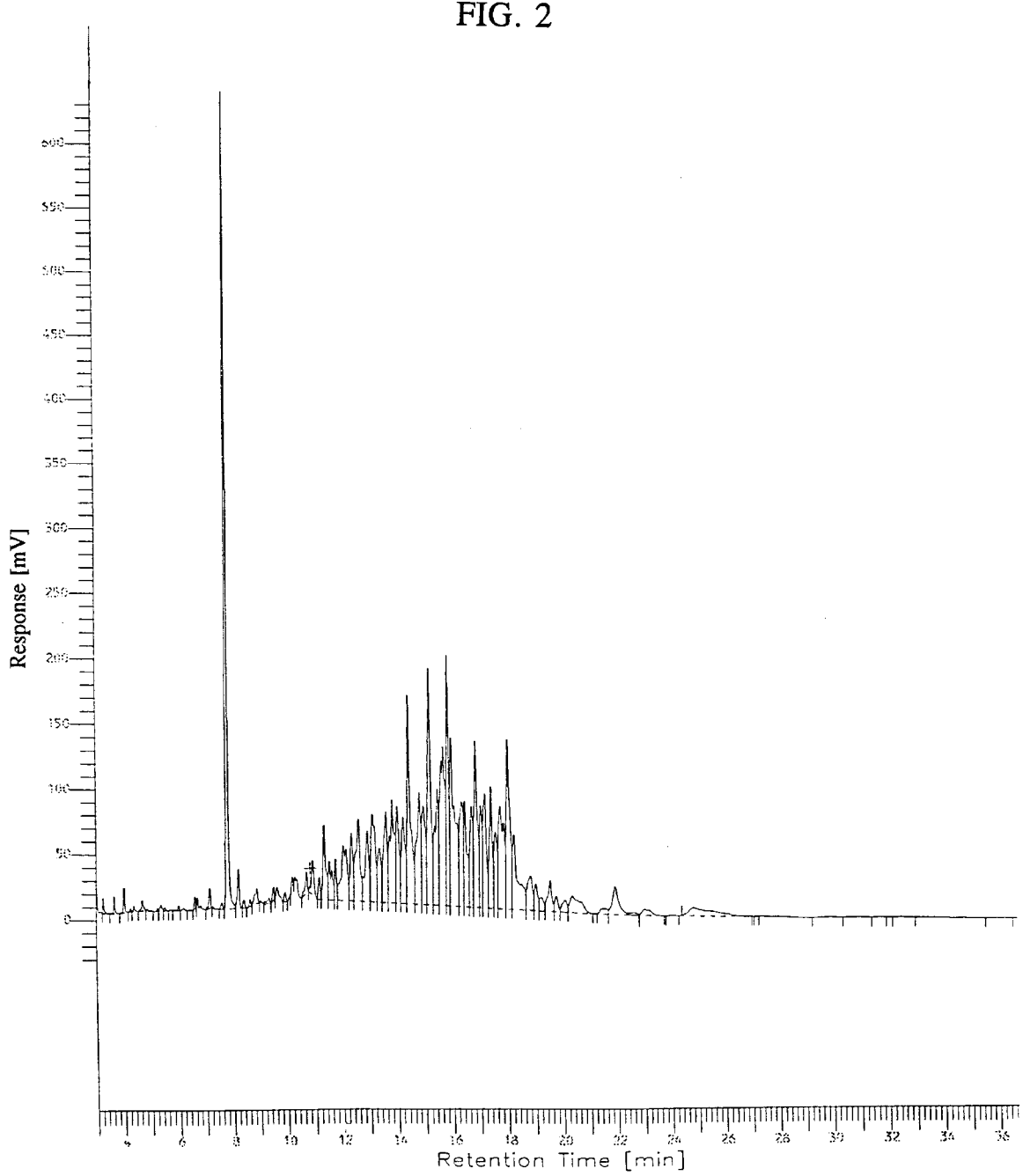
FIGS. 2–4 are gas chromatograms of a sample of soil contaminated with toxaphene before and after treatment with denitrifying bacteria.
Figure 3:
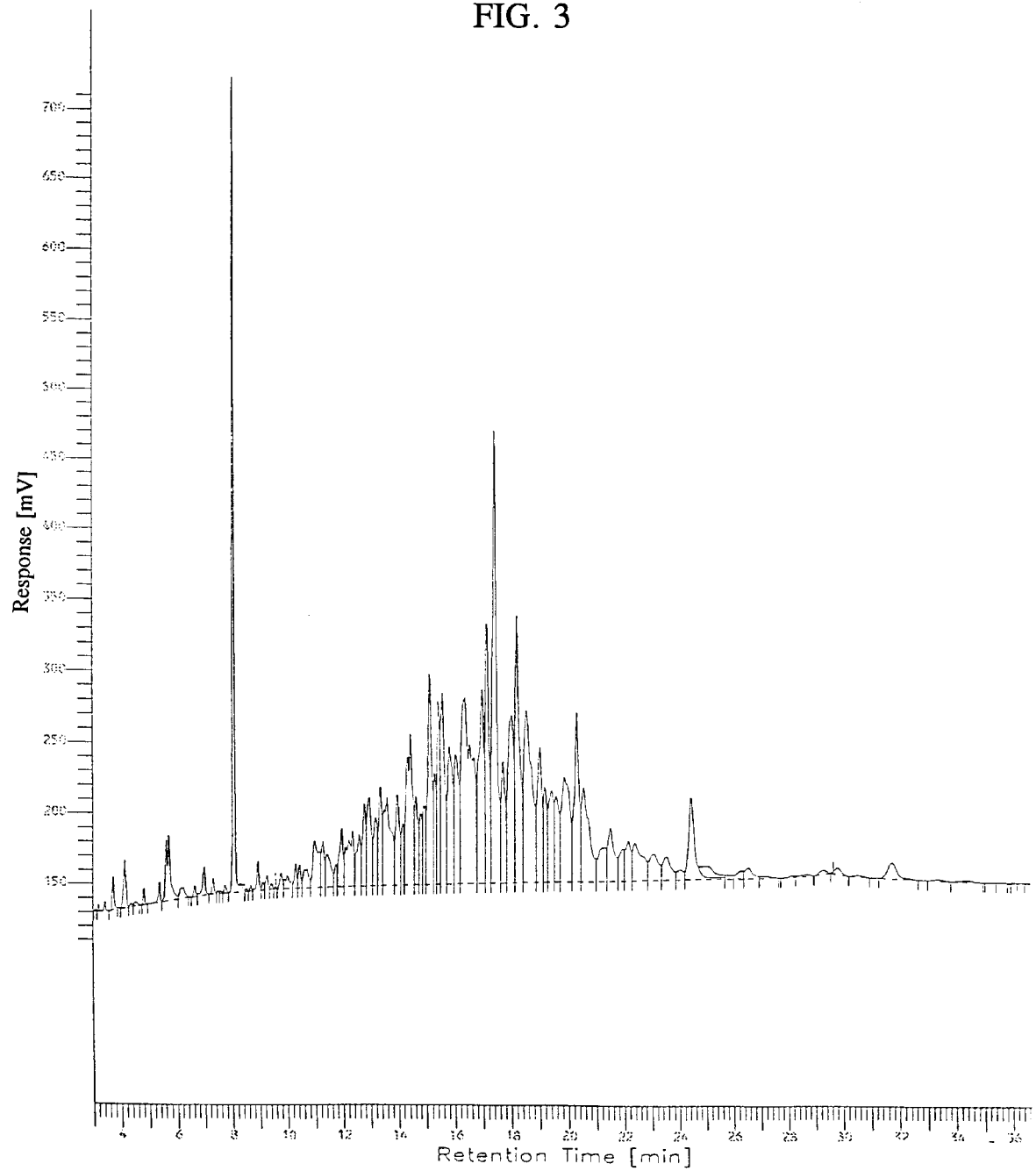
Figure 4:
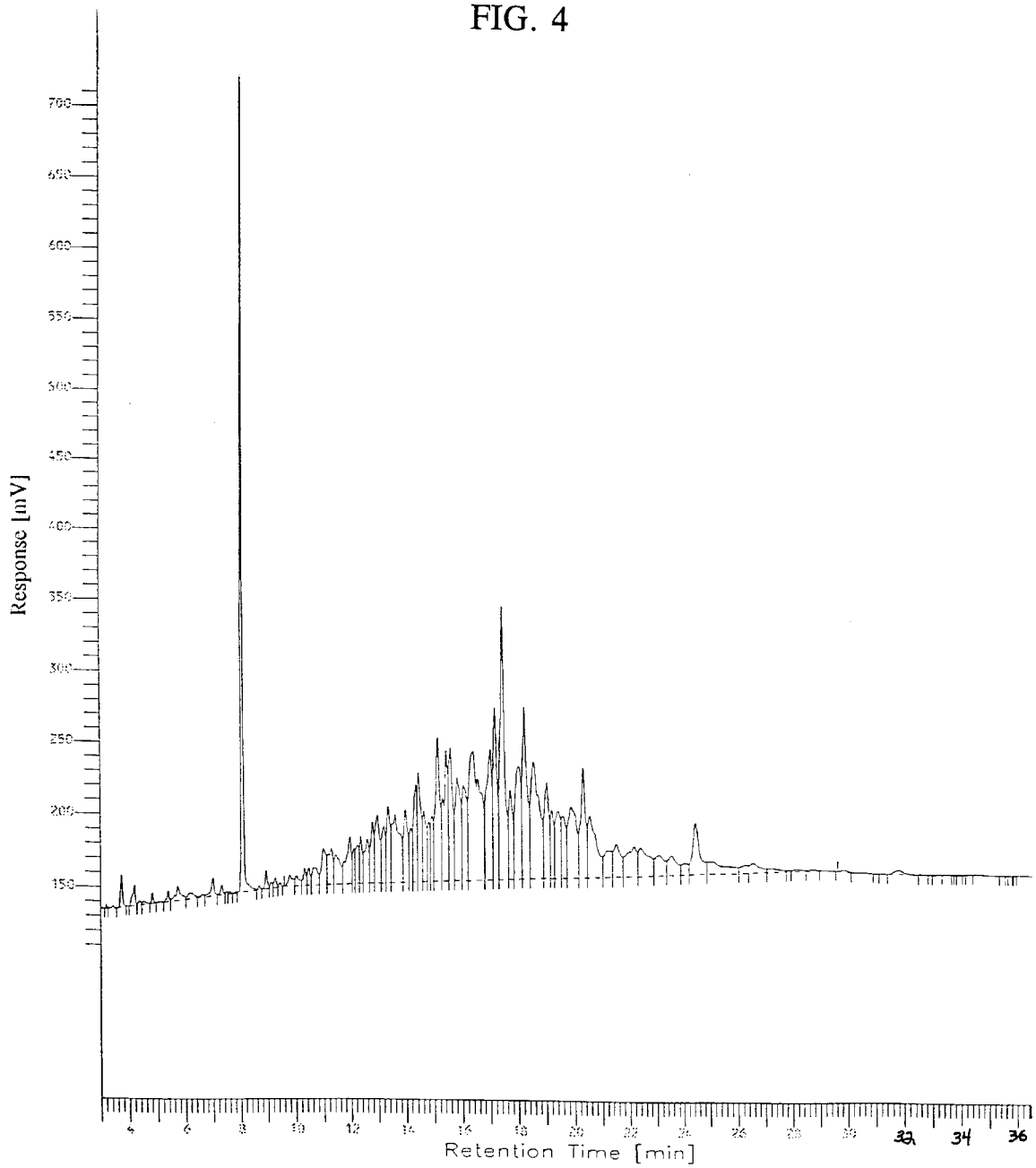
Figure 5:
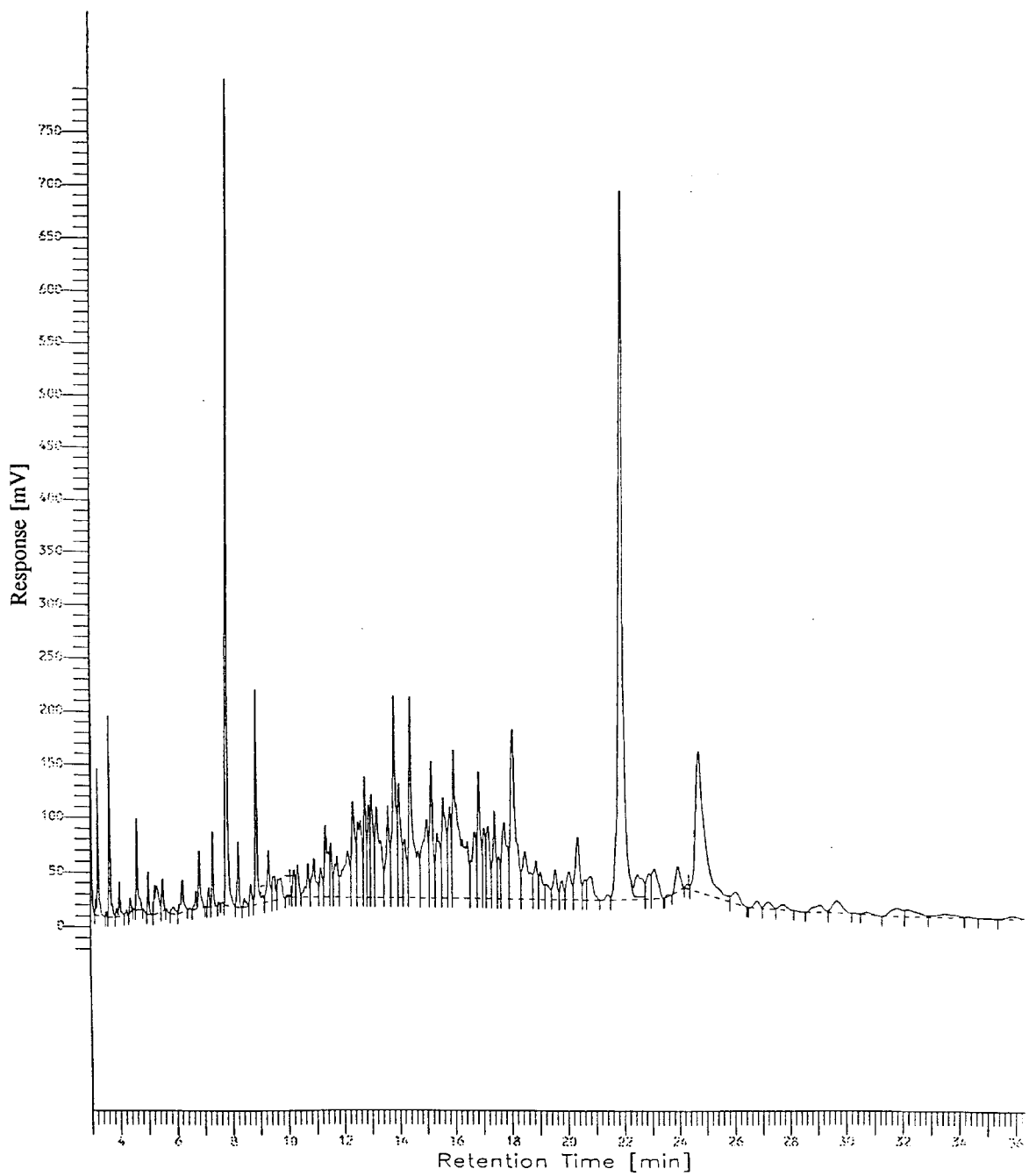
FIGS. 5–7 are gas chromatograms of a sample of soil contaminated with toxaphene before and after treatment with methanotrophic bacteria.
Figure 6:
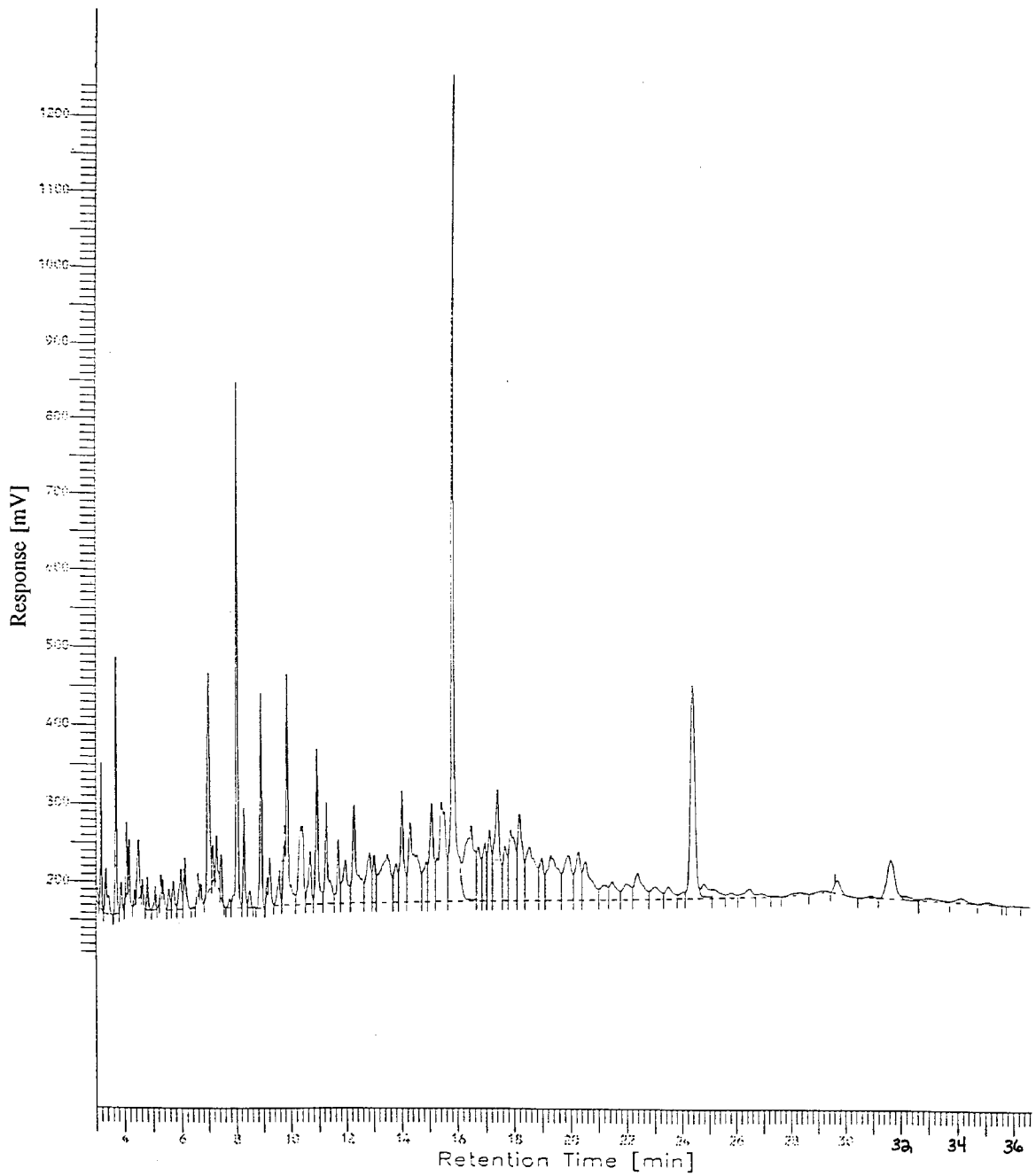
Figure 7:
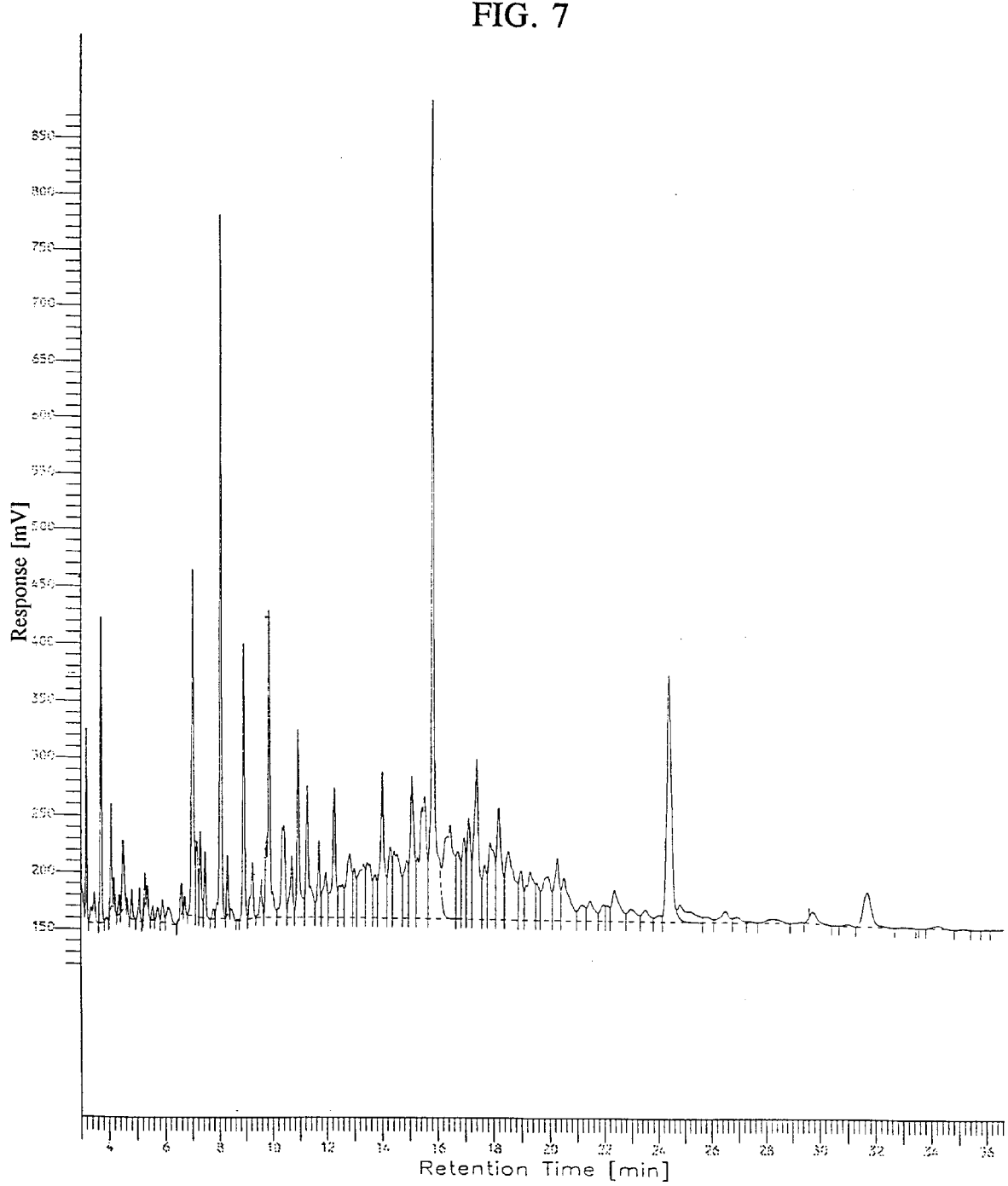
Figure 8:
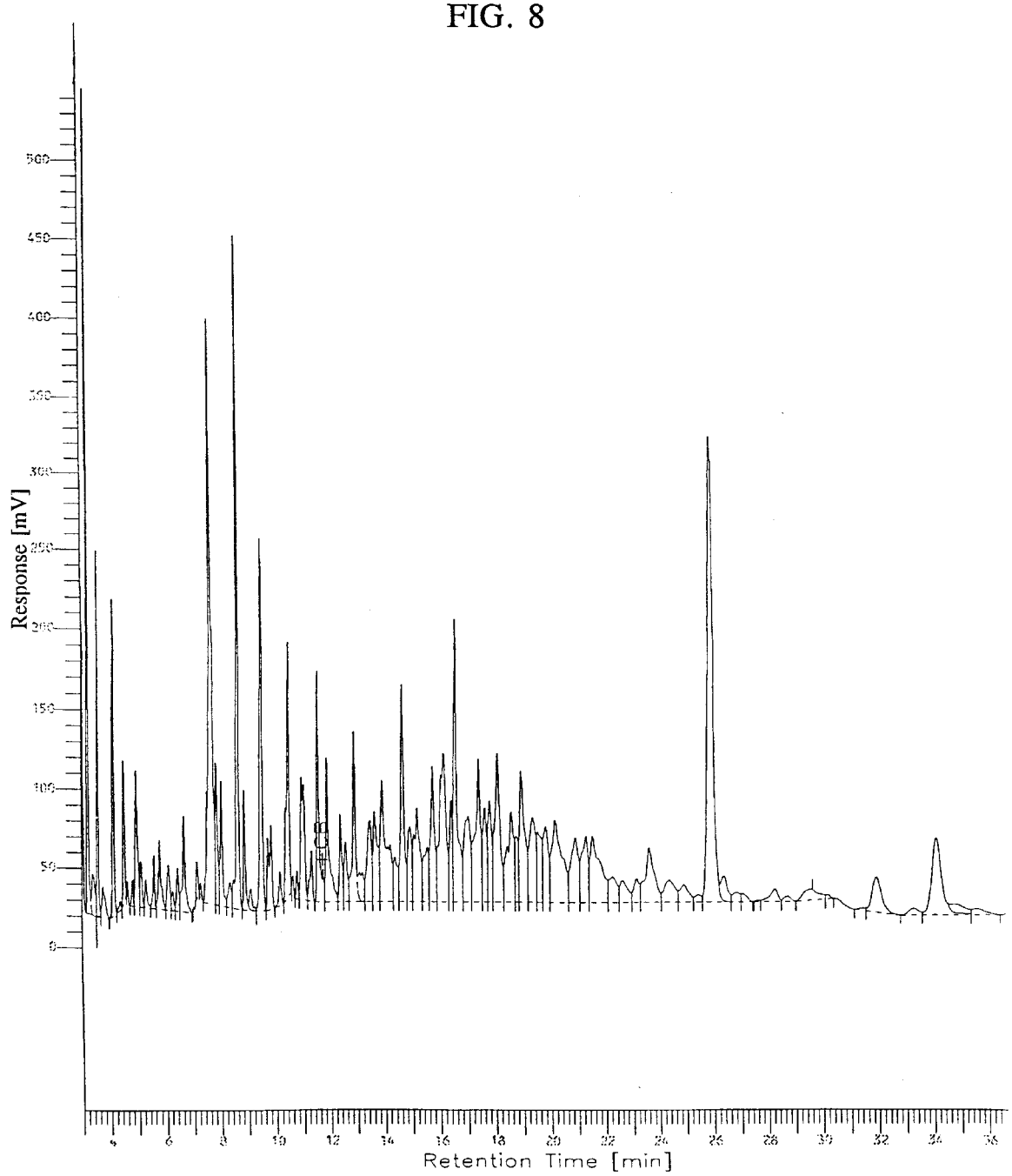
FIGS. 8–10 are gas chromatograms of a sample of soil contaminated with toxaphene before and after treatment with methanotrophic bacteria.
Figure 9:
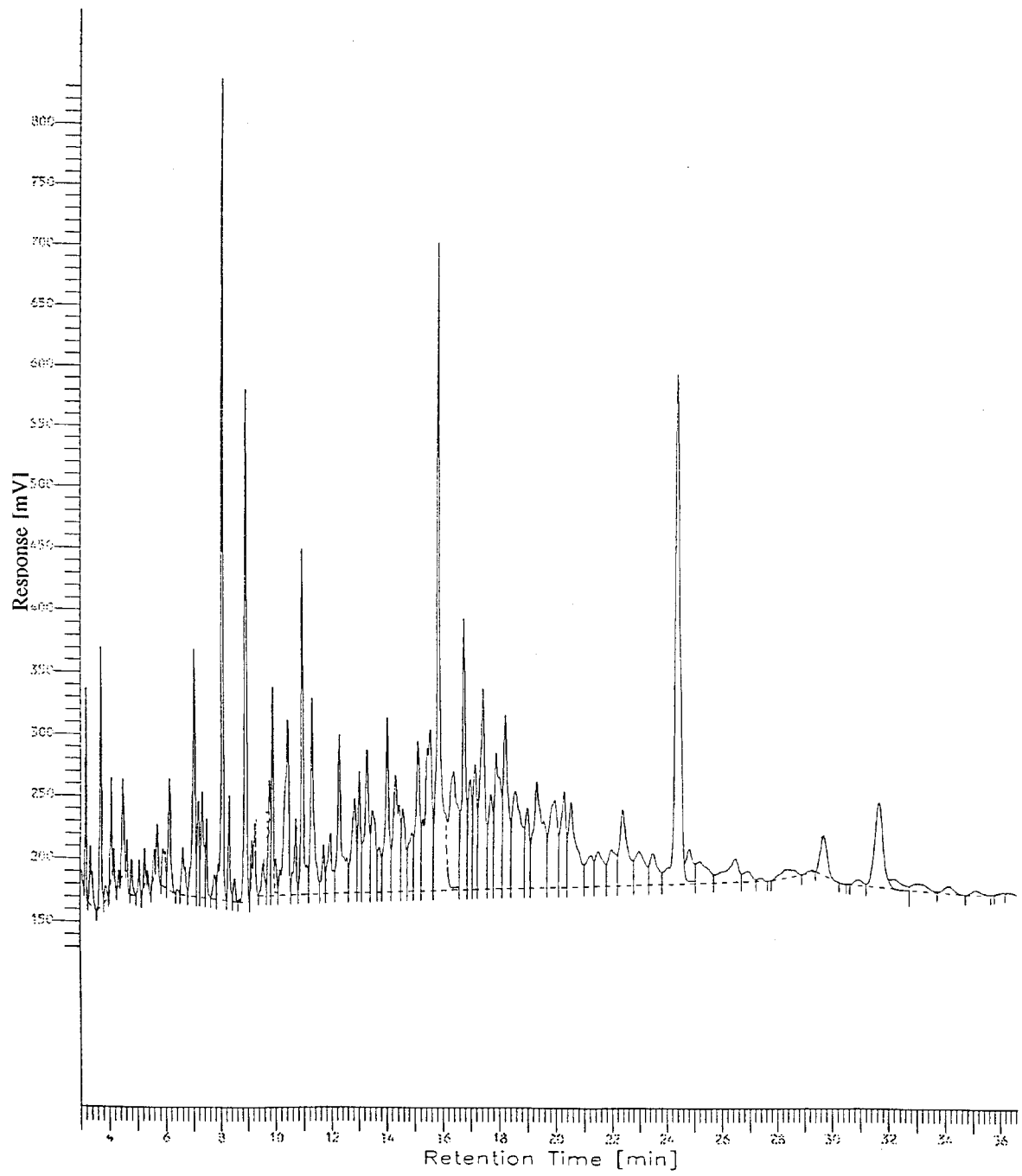
Figure 10:
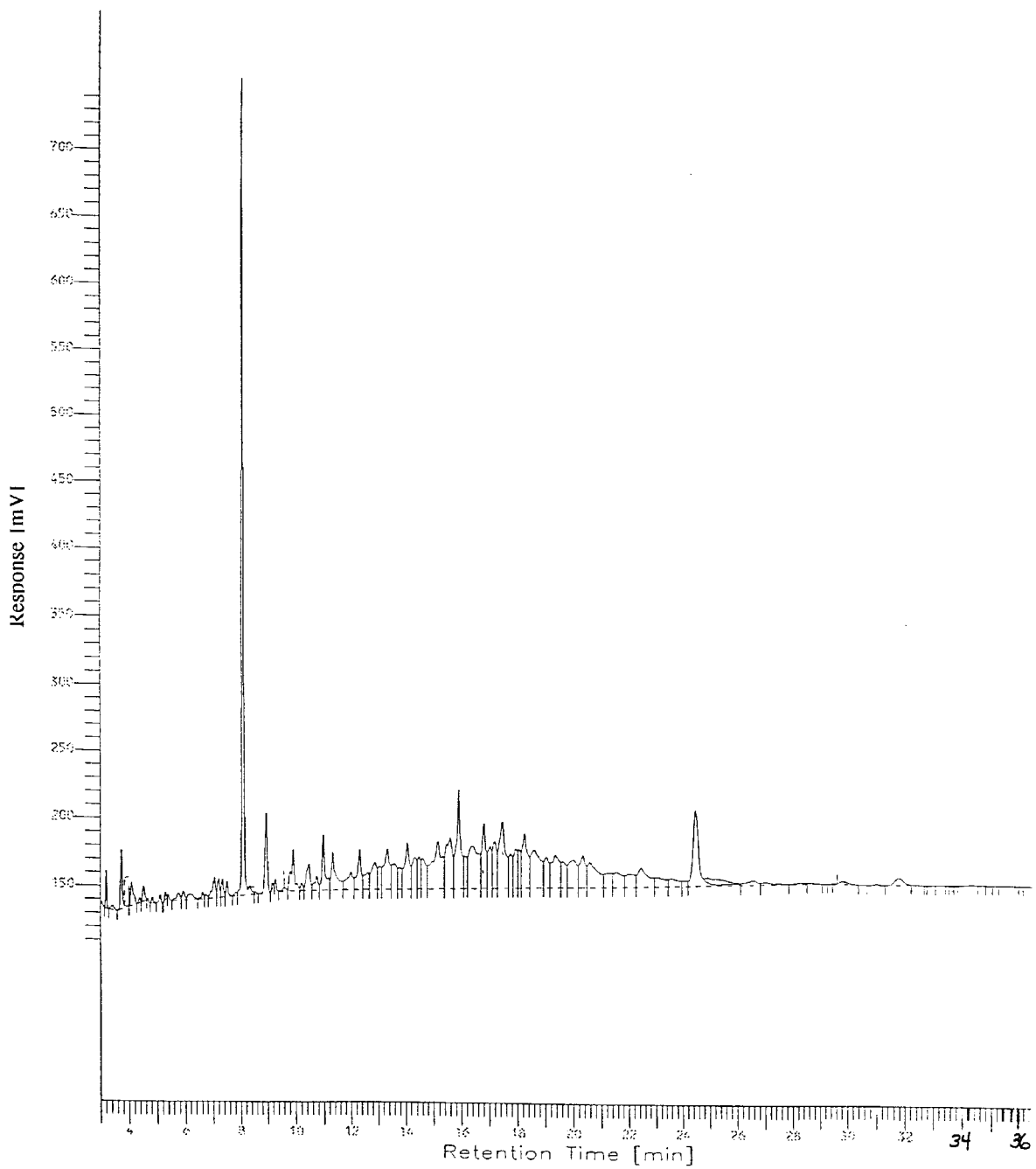
Figure 11:
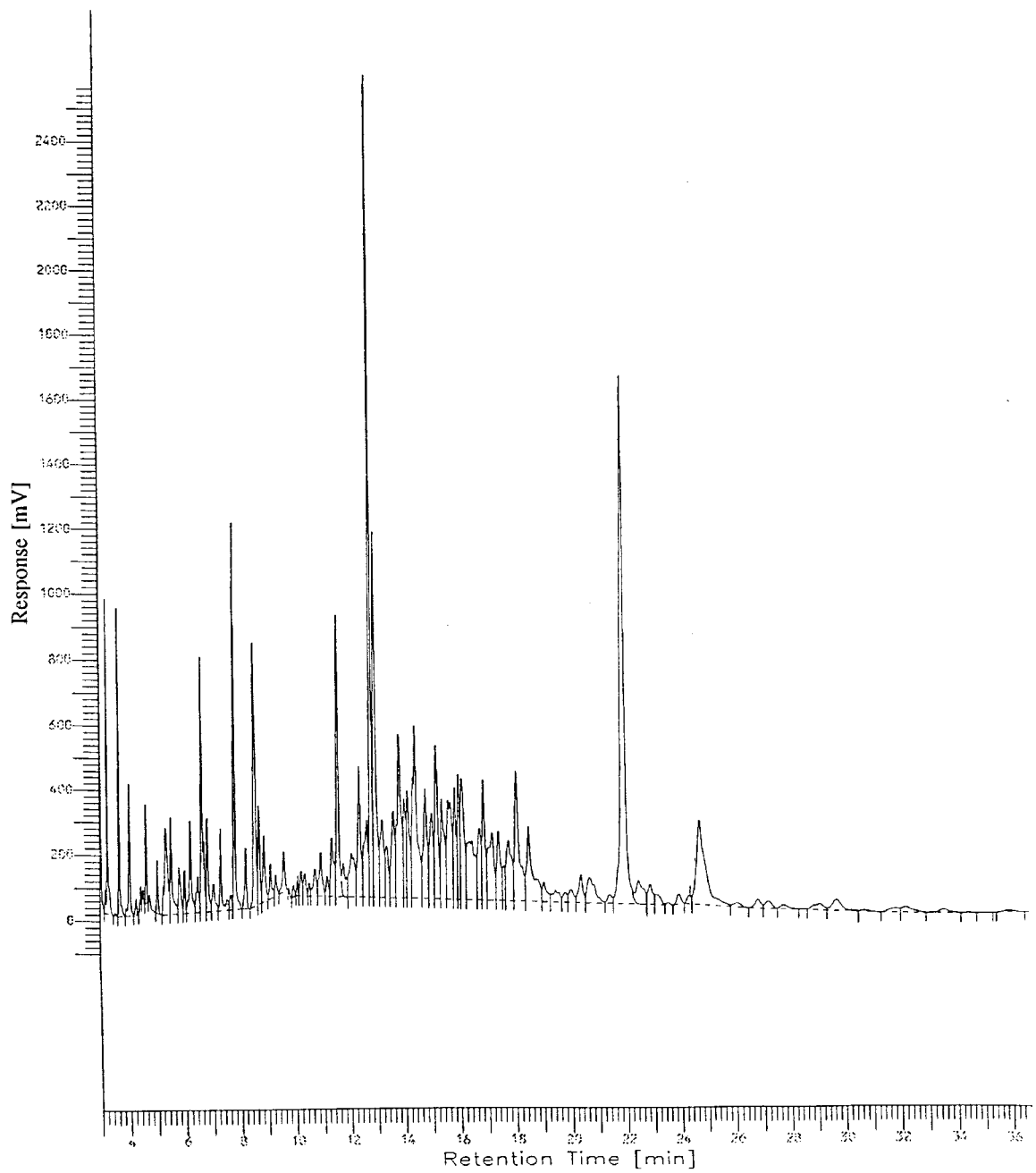
FIGS. 11–13 are gas chromatograms of a sample of soil contaminated with toxaphene before and after treatment with methanotrophic bacteria.
Figure 12:
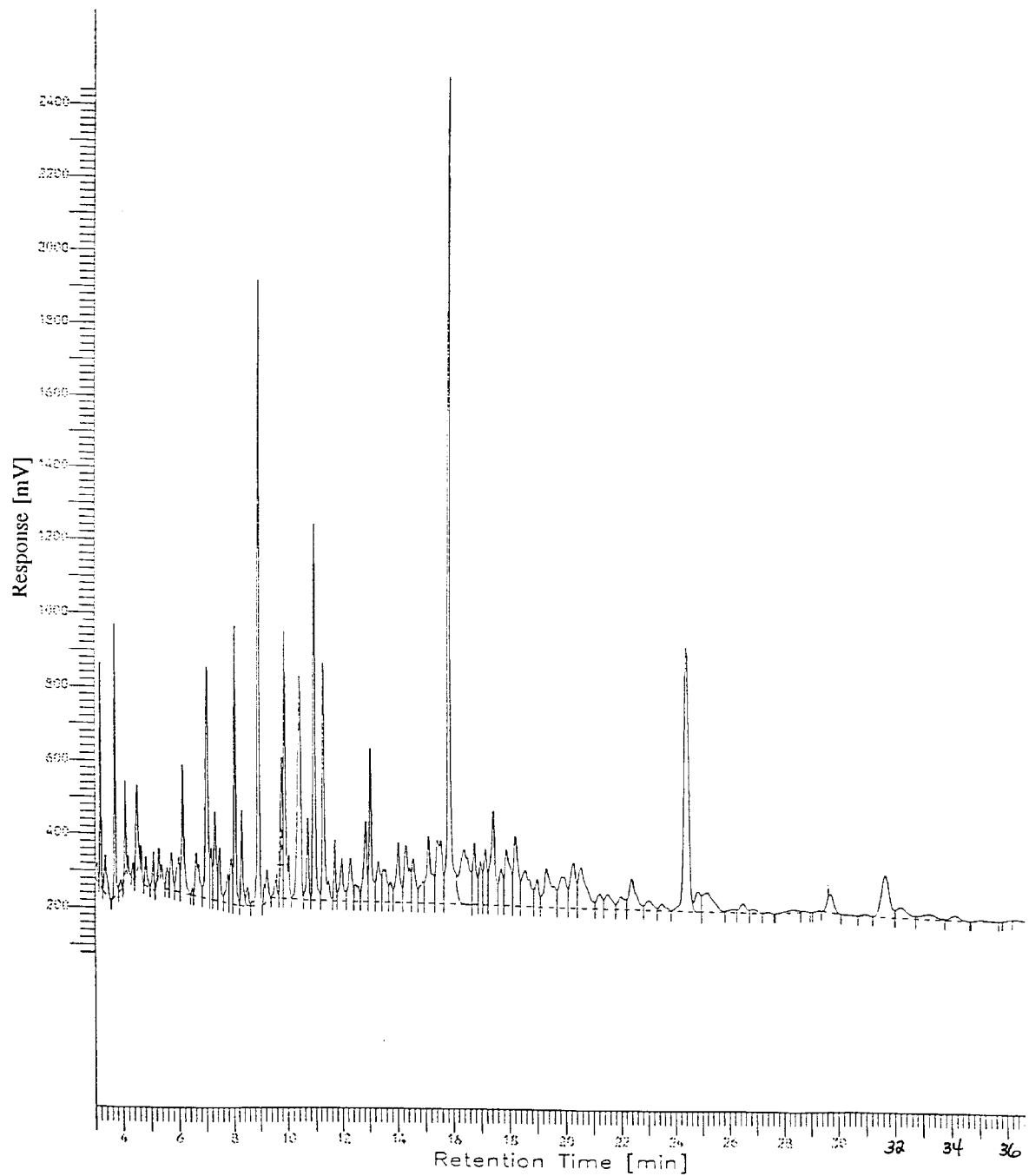
Figure 13:
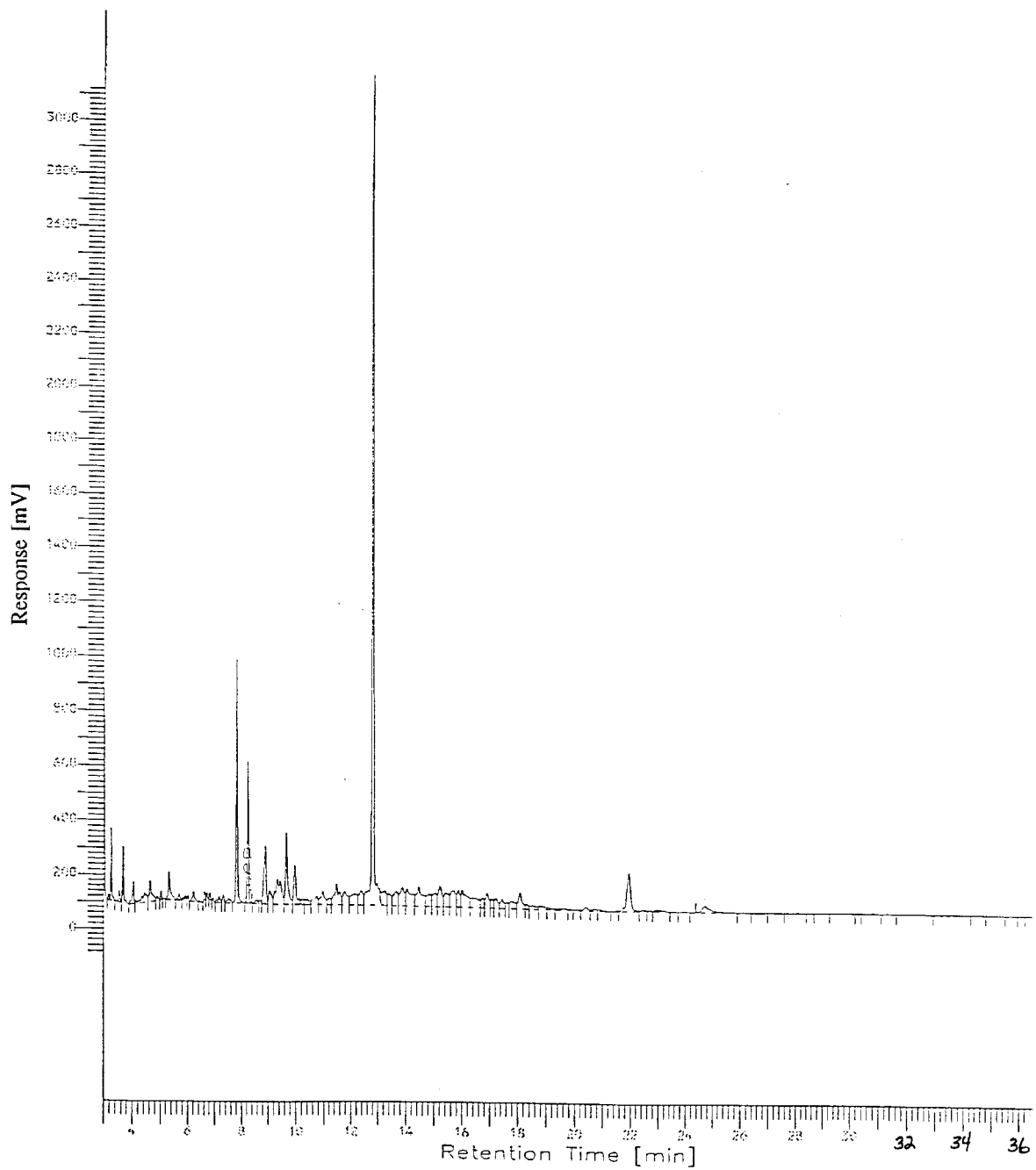

The samples were analyzed for toxaphene using EPA method 8080. Final time ($T_f$) soil samples were collected on day 144, at approximately the same locations and depths as the $T_O$ samples. The $T_f$ samples were split three ways and analyzed for: (1) toxaphene using EPA method 8080, (2) toxaphene by-products using EPA 8270, and (3) apparent toxaphene as described above. A confirmatory soil sample (DEN Middle) was collected at a depth of 6"–12" on day 224, and analyzed for toxaphene and toxaphene by-products using EPA method 8270. Method 8270 for toxaphene was used because it was suspected that by-products were interfering with the method 8080 toxaphene chromatogram and producing false positive toxaphene concentrations. Chromatograms were retained for each of the sampling events. FIG. 1 is the standard chromatogram of toxaphene. The results appear in Table 1 and FIGS. 2–4.

Analysis of the initial soil sample results using EPA method 8080 (Table 1) indicates that toxaphene concentration in this test plot increased or remained at nearly the same value throughout the course of the study. The only samples in which a marked decrease in toxaphene was measured ($\Delta T_O - T_c$) was in L1-A and L4-A. Analysis of the change in toxaphene concentrations between the final soil analysis and the final soil analysis after the florisil column cleanup ($\Delta T_f - T_c$) indicates a decrease in toxaphene concentrations in many cases, suggesting that other compounds interfered with the method and yielded false positive data. When a confirmation sample (DEN middle) was collected from the center of the plot at a depth of 6"–12" and analyzed for toxaphene using EPA method 8270, toxaphene concentrations were below detectable levels (Table 9). Chloride ion (Cl⁻) concentrations measured in the monitoring points increased slightly after 30 days (Table 6), but then fell to levels below initial concentrations by the end of the study. Analysis of the ground-water sample results from the downgradient monitoring well (Table 5) shows that dissolved phase toxaphene concentrations nearly doubled during the study and that inferring compounds caused some false positive data.

EXAMPLE 3

Degradation of Toxaphene by Methanotrophic Bacteria. A 20 foot by 20 foot test plot located within the area tested in Example 1 and approximately 60 feet due west of the denitrification test plot used in Example 2 was used to test for the degradation of toxaphene by methanotrophic bacteria. As for the denitrification plot, high toxaphene concentrations were the criterion for the placement of the pilot study area. A 5% methane/air mixture was delivered to the toxaphene impacted soils by using five foot deep injection points constructed of 0.75 inch (I.D.) black pipe. The injection pressure of the methane/air mixture was regulated so that the average injection rate per point was 0.5 SCFM.

Five methane/air injection points were installed in the upgradient portion of the plot. An "aerobic curtain" was created in the downgradient portion of the plot by installing five air-only injection points. The purpose of the air-only points was to introduce oxygen to the shallow groundwater to promote the aerobic degradation of any toxaphene by-products before they migrated out of the plot.

The methane cometabolism pilot study plot was constructed in a fashion similar to that of the denitrification test plot, including a sand bag and gravel berm. Also, four ground-water monitoring points (METHMP-1 through METHMP-4) were installed in the study area, and one recovery well (METH-MW) was located immediately downgradient of the study area. Ground-water samples were collected periodically from the recovery well and from the monitoring points in the plot. The samples were analyzed for dissolved chloride (Cl⁻) and nitrate (NO$_3^-$) using EPA method 300.0.

A ground-water sample was collected from the recovery well on day 81, and analyzed for toxaphene using EPA method 608. At the end of the field pilot study (day 144), another ground-water sample was collected from the recovery well. The sample was split three ways and analyzed for: (1) toxaphene using EPA method 8080, (2) toxaphene by-products using EPA 8270, and (3) apparent toxaphene as previously defined.

Initial time ($T_O$) soil samples were collected with a decontaminated, stainless steel hand auger on day 1. The sample locations were distributed throughout the test plot at two different depths for each location: A (6"–12") and B (18"–24"). The locations were designated L7 through L12.

The samples were analyzed for toxaphene using EPA method 8080. Final time ($T_f$) soil samples were collected on day 144, at approximately the same locations and depths as the $T_O$ samples. The $T_f$ samples were split three ways and analyzed for: (1) toxaphene using EPA method 8080, (2) toxaphene by-products using EPA 8270, and (3) apparent toxaphene using the method previously discussed. Confirmatory soil samples were collected on day 224, and analyzed for toxaphene and toxaphene by-products using EPA method 8270. One sample was collected near the methane/air injection points (METH NE Corner) and one was obtained near the aerobic curtain (METH Aerobic Zone). Chromatograms were retained for each of the sampling events. The results appear in Table 2 and FIGS. 5–13.

Analysis of the initial soil sample results from this plot using EPA method 8080 (Table 2) indicates that toxaphene concentrations increased in some locations of the plot and decreased in other locations. A marked decrease in toxaphene was measured ($\Delta T_O - T_c$) in sample L8-A (>90,000 µg/kg). Analysis of the change in toxaphene concentrations between the final soil analysis and the final soil analysis after the florisil column cleanup ($\Delta T_f - T_c$) indicates a decrease in toxaphene concentrations in every sample but L7-A. These data suggest that other compounds interfered with the method and yielded false positive data. When confirmation samples (METH NE Corner and METH aerobic zone) were collected from the plot and analyzed for toxaphene using EPA method 8270, toxaphene concentrations were below detectable levels (Table 4). Chloride ion (Cl⁻) concentrations measured in the monitoring points were higher initially than the denitrification plot and nearly doubled in METHMP-1 and METHMP-2 after approximately 30 days (Table 7). Analysis of the ground-water sample results from the downgradient monitoring well shows that toxaphene concentrations were over an order of magnitude less at the end of the study than at the beginning (Table 5).

EXAMPLE 4

Controlled Experiment. A 20 foot by 20 foot square control plot was placed near the pilot study areas used in Examples 2 and 3. The control plot was not bermed and did not have any ground-water monitoring points, injection points, or a downgradient recovery well. The initial intention was to leave this plot undisturbed throughout the study.

Initial time ($T_O$) soil samples were collected with a decontaminated, stainless steel hand auger on day 1. The sample locations were distributed throughout the test plot at two different depths for each location: A (6"–12") and B (18"–24"). The locations were designated C1 and C2.

The samples were put on ice and shipped to the laboratory under chain of custody. The soils were then analyzed for toxaphene by EPA method 8080. Final time ($T_f$) soil samples were collected on day 144, at approximately the same locations and same depths as the $T_O$ samples.

The $T_f$ samples were analyzed using the same methods discussed above for the denitrification and methane cometabolism plots. A confirmatory control sample was collected on day 224, in an area upgradient from the control plot and analyzed for toxaphene and toxaphene by-products using EPA method 8270. Chromatograms were retained for each of the sampling events. Results appear in Table 3 and FIGS. 14–16.

Analysis of the initial soil sample results from the control plot area using EPA method 8080 (Table 3) indicates that toxaphene concentrations increased in every sample but C2-B (Table 3). The data also show that interfering compounds were present in the control plot soil samples. When a confirmation sample (TOX test) was obtained from an area upgradient of the control plot and analyzed for toxaphene using EPA method 8270, toxaphene was below detectable levels (Table 4).

EXAMPLE 5

The confirmatory soil samples collected in Examples 2, 3, and 4 were analyzed for toxaphene and toxaphene by-products using EPA method 8270. Sample "DEN Middle" was collected at a depth of 6"–12" in the denitrification test plot of Example 2. Additional samples were taken near the methane/air injection points ("METH NE Corner") and near the aerobic curtain ("METH Aerobic Zone") in the methane cometabolism test plot of Example 3. Sample "TOX" was taken in an area upgradient from the control test plot of Example 4. Results appear in Table 4.

EXAMPLE 6

The ground water monitored in the test plots of Examples 2, 3, and 4 was analyzed. The results in Table 5 show a significant decrease in the toxaphene levels in the methane cometabolism test plot (Example 3). The increase in toxaphene concentration seen the denitrification test plot (Example 2) may have been due to increased solubility of the degraded toxaphene compounds.

EXAMPLE 7

Chloride concentrations were measured in the denitrification test plots of Examples 2 and 3. Results appear in Tables 6 and 7.

EXAMPLE 8

The confirmatory soil samples taken in Examples 2, 3, and 4 were analyzed for chemical content. Compounds that were tentatively identified as being present are listed in Table 9. Sample IDs 1–5 in Table 9 refer to the following: Sample ID 1=METH NE Corner 6–12"; Sample ID 2=METH NE Corner 18–24"; Sample ID 3=METH Aerobic Zone; Sample ID 4=DEN Middle; and Sample ID 5=TOX Control Test.

Discussion of Toxaphene Degradation

Because the presence of interfering compounds caused false positive data when quantifying toxaphene with EPA method 8080, the best data for measuring actual toxaphene degradation during these field trials is the chromatograms. The toxaphene chromatogram is a complex mixture of many peaks with a wide range of GC retention times (FIG. 1). As the toxaphene molecule degrades the chromatographic fingerprint may be altered in several ways. As the fraction of less-chlorinated toxaphene components/by-products increases (compounds that have shorter GC retention times), there will be a shift in the chromatogram to the left. An increased concentration of interfering by-products will also result in an elevated baseline. Analysis of the chromatogram before and after a cleanup procedure (i.e., silica gel or florisil) also provides evidence that degradation occurred and that interfering by-products were removed with the cleanup.

Analysis of the toxaphene chromatogram (EPA method 8080) from sample L1-B illustrates the overall patterns observed in the denitrification plot. Chromathograms from this plot exhibited relatively few alterations in the toxaphene fingerprint as compared to the toxaphene standard chromatogram (FIGS. 1–4). This is in contrast to the weathered/shifted chromatogram examples from the methane cometabolism plot (FIGS. 5–13). Note that the example chromatograms from the methane cometabolism plot exhibit the following characteristics: (1) an increase in the number and size of peaks having shorter GC retention times; (2) an elevated baseline between initial ($T_O$) and final samples ($T_r$); and (3) the cleanup procedure removed many of the interfering compounds.

When the confirmation soil samples were analyzed for toxaphene and toxaphene by-products using EPA method 8270 (GC/MS method), several tentatively identified interfering compounds/by-products were identified (Table 8) with retention times ranging from 2.7 to 9.2 minutes. These compounds appear to the left of the standard toxaphene fingerprint and have solubility values greater than toxaphene.

Figure 14:
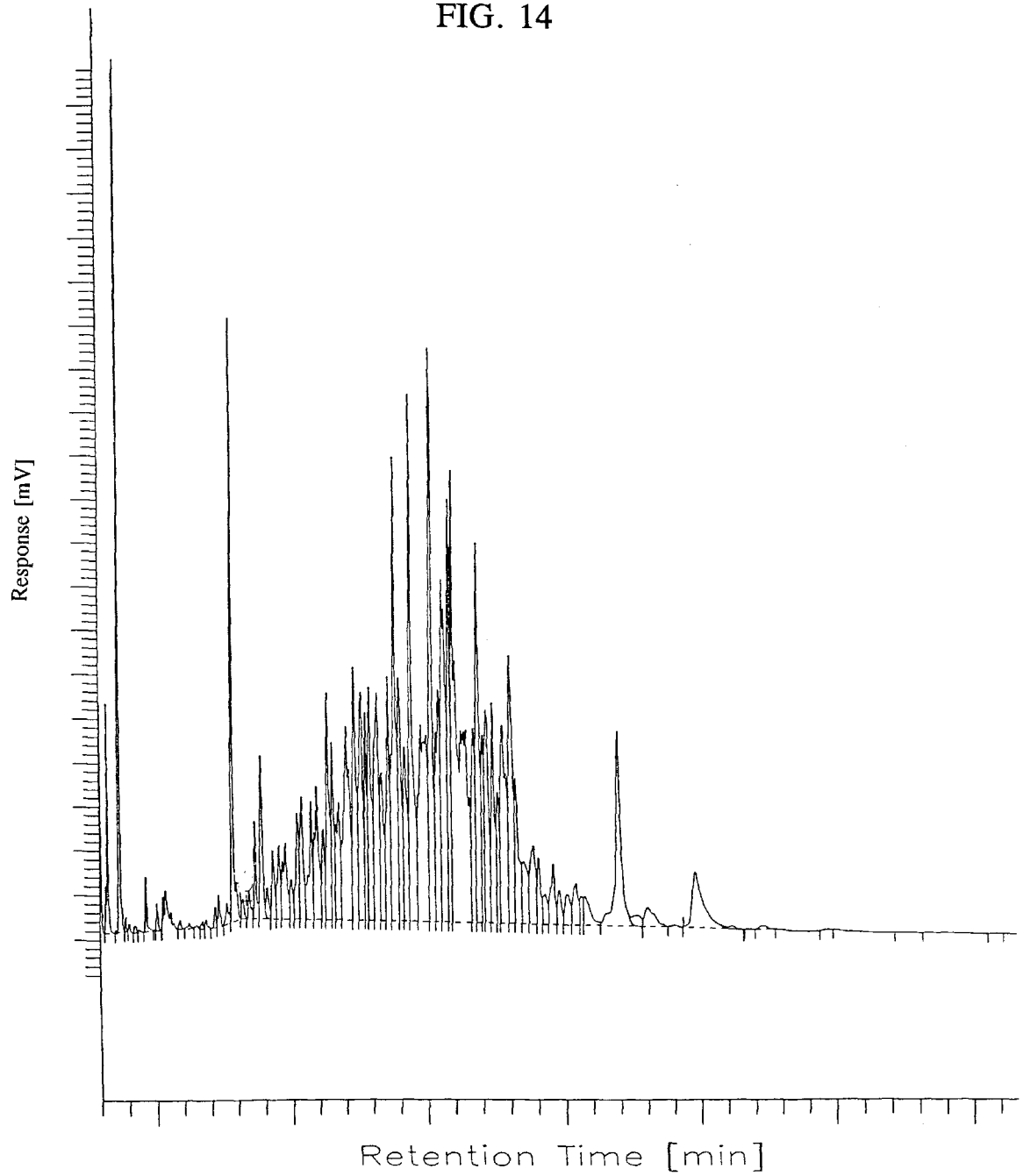
FIGS. 14–16 are gas chromatograms of a control sample of soil contaminated with toxaphene.
Figure 15:
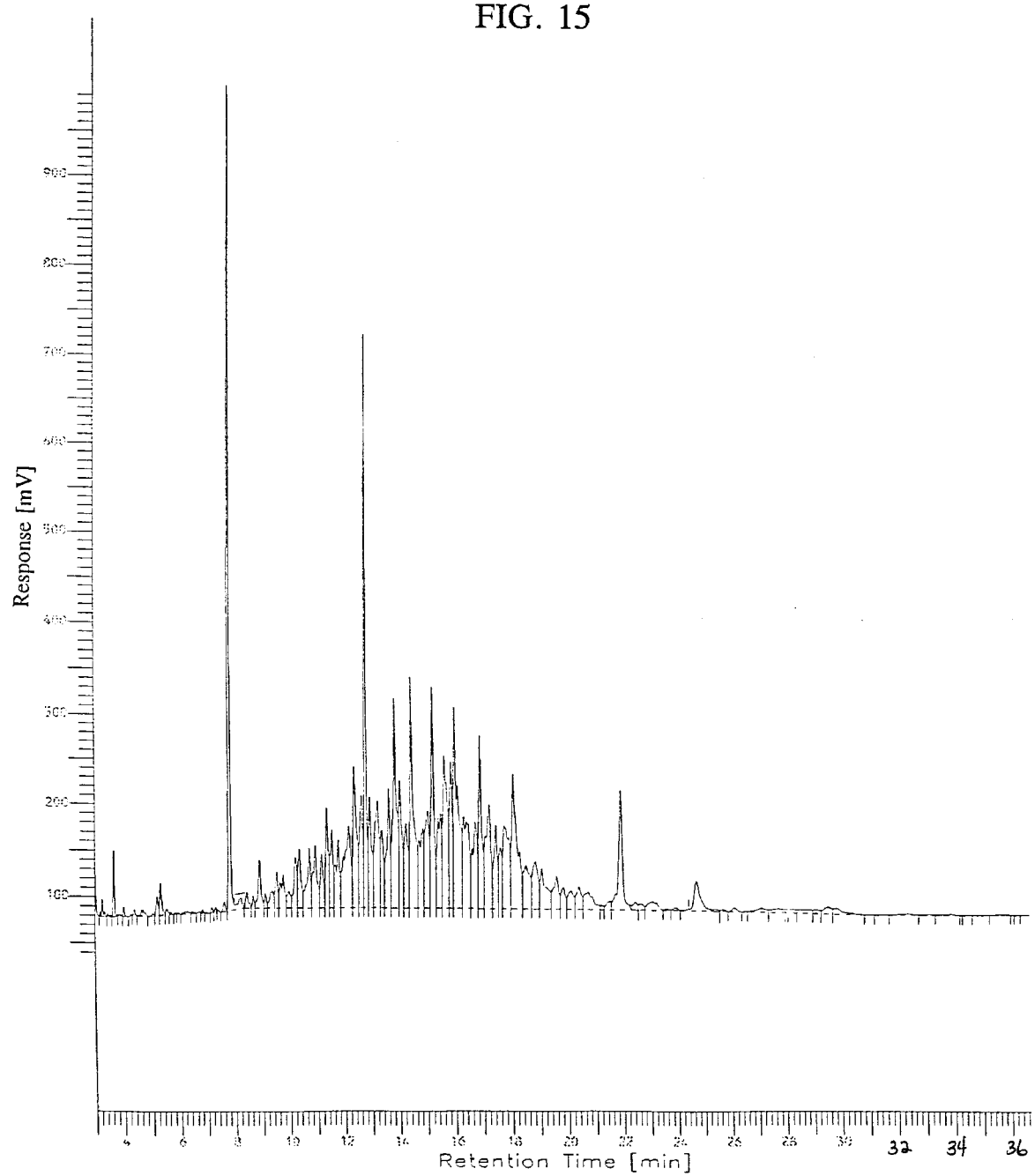
Figure 16:
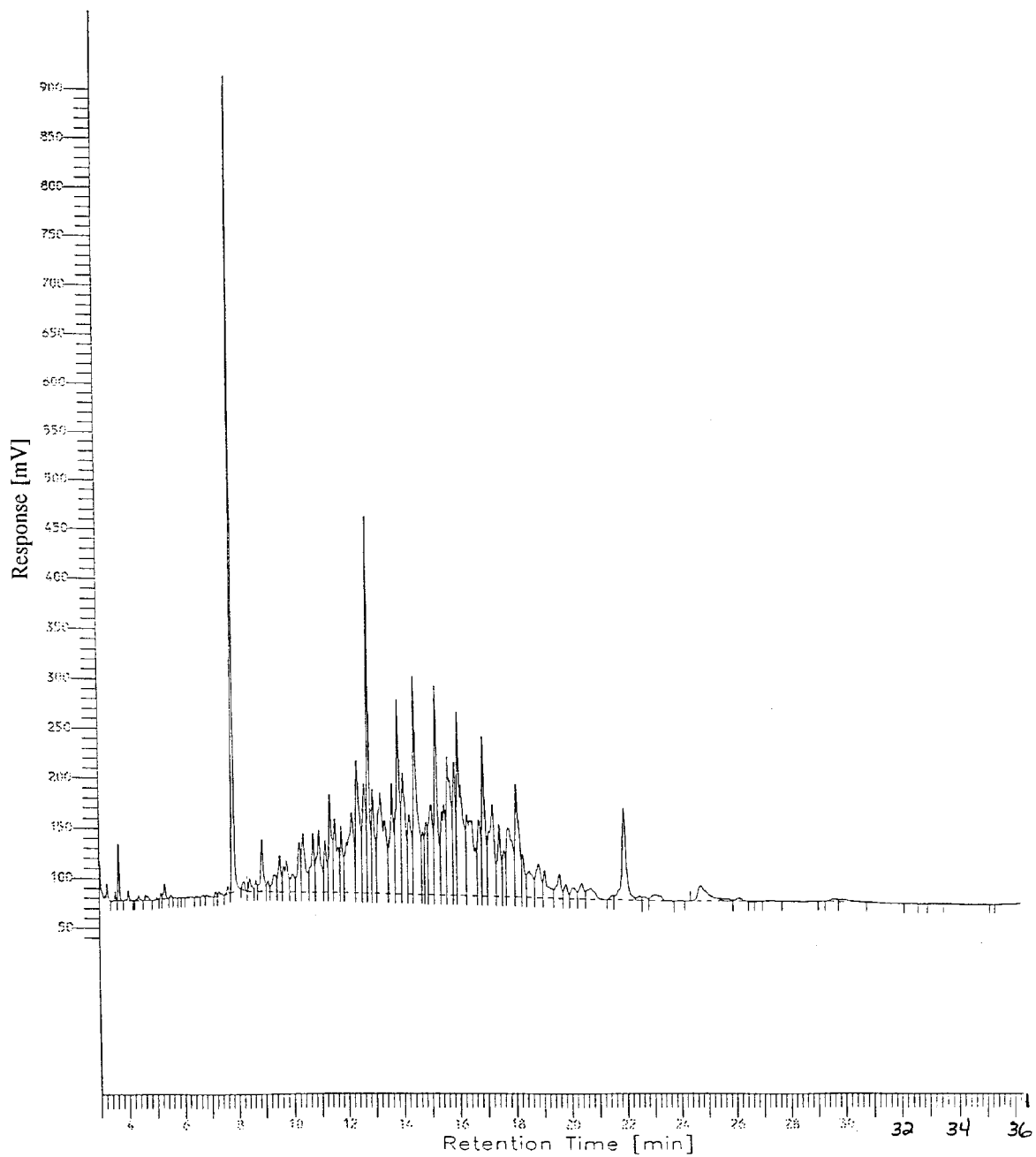

Note that in the control test plot the shift between the initial time and final time toxaphene concentrations was only 5% (Table 3). These data indicate that the control plot conditions were in fact well controlled. The good control in this plot is confirmed by chromatographic evidence from sample C1-B (FIGS. 14–16). There were few alterations in the toxaphene fingerprint from initial time ($T_O$) to final time ($T_f$) and the chromatograms reflected the characteristic pattern of the technical toxaphene example chromatogram (FIG. 1).

Based on the chromatographic evidence, the toxaphene molecule did appear to be degraded/biotransformed in the denitrification plot. However, analysis of the chromatograms from the toxaphene-contaminated soils treated in the methane cometabolism plot indicates a much greater extent of degradation. The denitrification plot failure is only an apparent failure due to a function of hydrostratigraphy.

Our ability to accurately quantify toxaphene in the soils during this field pilot study was limited by EPA method 8080. While this method is designed for determining the concentration of technical grade or relatively unweathered toxaphene, it does not seem to be appropriate for quantifying degraded/weathered toxaphene concentrations. The presence of more soluble by-products in the sample and compounds that interfere with the chromatogram can yield false positive toxaphene concentrations. Even the florisil column cleanup procedure did not remove all of the interference. Therefore, increases in apparent toxaphene concentrations as reported in the tables are not an indication that the remediation method failed or was ineffective. The ineffectiveness of the remediation method is more appropriately evaluated by changes in the chromatograms, especially the changes in the chromatograms after the florisil column cleanup procedure. Preliminary results indicate that a GC/MS method, like EPA 8270 or 8260 may be better suited for quantifying degraded toxaphene concentrations in the field.

Analysis of the chromatograms, especially those from the methane cometabolism plot that show significant alterations between initial and final time samples, indicates that the soils no longer contain technical toxaphene as regulated. Instead, we are dealing with degraded/weathered toxaphene fractions that are more susceptible to aerobic microbial degradation. Interference from by-products can also occur right in the middle of the chromatogram. The chromatogram does not necessarily have to be shifted left to show degradation.

TABLE 1

Denitrification Pilot Study Soil Samples

| Sample ID | Toxaphene Concentration ($\mu g/kg$) | | | | | |
|---|---|---|---|---|---|---|
| | Initial ($T_o$) | Final ($T_f$) | After Florisil Cleanup ($T_c$) | Δ $T_o - T_f$ | Δ $T_f - T_c$ | Δ $T_o - T_c$ |
| L1-A | 190,000 | 18,000 | 15,000 | 172,000 | 3000 | 175,000 |
| L1-B | 230,000 | 320,000 | 190,000 | −90,000 | 130,000 | 40,000 |
| L2-A | 310,000 | 530,000 | 540,000 | −220,000 | −10,000 | −230,000 |
| L2-B | 190,000 | 230,000 | 220,000 | −40,000 | 10,000 | −30,000 |
| L3-A | 91,000 | 230,000 | 240,000 | −139,000 | −10,000 | −149,000 |
| L3-B | 280,000 | 280,000 | 230,000 | 0 | 50,000 | 50,000 |
| L4-A | 220,000 | 47,000 | 34,000 | 173,000 | 13,000 | 186,000 |
| L4-B | 40,000 | 90,000 | 66,000 | −50,000 | 24,000 | −26,000 |
| L5-A | 75,000 | 190,000 | 200,000 | −115,000 | −10,000 | −125,000 |
| L5-B | 31,000 | 40,000 | 37,000 | −9,000 | 3,000 | −6,000 |
| L6-A | 13,000 | 35,000 | 30,000 | −22,000 | 5,000 | −17,000 |
| L6-B | 95,000 | 140,000 | 160,000 | −45,000 | −20,000 | −65,000 |

TABLE 2

Methane Cometabolism Pilot Study Soil Samples

Toxaphene Concentration (µg/kg)

| Sample ID | Initial ($T_0$) | Final ($T_f$) | After Florisil Cleanup ($T_c$) | Δ $T_0 - T_f$ | Δ $T_f - T_c$ | Δ $T_0 - T_c$ |
|---|---|---|---|---|---|---|
| L7-A | BDL | 15,000 | 22,000 | −15,000 | −7,000 | −22,000 |
| L7-B | 11,000 | 35,000 | 35,000 | −24,000 | 0 | −24,000 |
| L8-A | 130,000 | 53,000 | 35,000 | 77,000 | 18,000 | 95,000 |
| L8-B | 40,000 | 48,000 | 28,000 | −8,000 | 20,000 | 12,000 |
| L9-A | 43,000 | 41,000 | 31,000 | 2,000 | 10,000 | −12,000 |
| L9-B | BDL | 5,900 | 3,500 | −5,900 | 2,400 | −3,500 |
| L10-A | 76,000 | 130,000 | 110,000 | −54,000 | 20,000 | −34,000 |
| L10-B | 75,000 | 73,000 | 56,000 | 2,000 | 17,000 | 19,000 |
| L11-A | 4,500 | 41,000 | 35,000 | −36,500 | 6,000 | −30,500 |
| L11-B | BDL | BDL | BDL | 0 | 0 | 0 |
| L12-A | 9,700 | 43,000 | 33,000 | −33,300 | 10,000 | −23,300 |
| L12-B | BDL | 21,000 | 16,000 | −21,000 | 5,000 | −16,000 |

TABLE 3

Control Plot Soil Samples

Toxaphene Concentration (µg/kg)

| Sample ID | Initial ($T_0$) | Final ($T_f$) | After Florisil Cleanup ($T_c$) | Δ $T_0 - T_f$ | Δ $T_f - T_c$ | Δ $T_0 - T_c$ |
|---|---|---|---|---|---|---|
| C1-A | 62,000 | 320,000 | 200,000 | −258,000 | 120,000 | −138,000 |
| C1-B | 150,000 | 270,000 | 210,000 | −120,000 | 60,000 | −60,000 |
| C2-A | 200,000 | 1,300,000 | 1,200,000 | $-1.1 \times 10^6$ | 100,000 | $-1.0 \times 10^6$ |
| C2-B | 3,100,000 | 1,900,000 | 1,300,000 | $1.2 \times 10^6$ | $1.77 \times 10^6$ | $2.97 \times 10^6$ |

TABLE 4

Confirmatory Soil Samples Collected

| Sample ID | Toxaphene Concentration |
|---|---|
| METH NE Corner 6–12" | ND |
| METH NE Corner 18–24" | ND |
| DEN Middle | ND |
| TOX Control Test | ND |

ND = not detected

TABLE 5

Ground-Water Samples from Denitrification and Methane Cometabolism Recovery Wells Toxaphene Concentration (µg/L)

| Example | Initial ($T_0$) | Final ($T_f$) | After Florisil Cleanup ($T_c$) | Δ $T_0 - T_f$ | Δ $T_f - T_c$ | Δ |
|---|---|---|---|---|---|---|
| 2 | 1,300 | 2,300 | 2,100 | −1,000 | 200 | −800 |
| 3 | 31 | 7.0 | 2.6 | 24 | 4.4 | 28.4 |

TABLE 6

Chloride (Cl) Concentrations in Denitrification Test Plot (reported in mg/L)

| | Day | | | | |
|---|---|---|---|---|---|
| Sample ID | 30 | 44 | 58 | 85 | 143 |
| DENMP-1 | 24.1 | 19 | 61.5 | 24.2 | 23 |
| DENMP-2 | 25.3 | 35.1 | — | — | 13 |
| DENMP-3 | 23.8 | 18 | 57.5 | 16.1 | 15 |
| DENMP-4 | 20.1 | 15.7 | 51.5 | 21 | 15 |
| DEN-MW | — | 66.6 | — | — | 42 |

TABLE 7

Chloride (C) Concentrations in Methane Cometabolism Test Plot (reported in mg/L)

| Sample ID | 30 | 44 | 58 | 85 | 143 | 224 (before/after purging) |
|---|---|---|---|---|---|---|
| METHMP-1 | 49.9 | 141.5 | 82.3 | 82.41 | 150 | 64/71 |
| METHMP-2 | 286.3 | 408.6 | 455.9 | 425.1 | 195 | 41/300 |
| METHMP-3 | 76.7 | 84.4 | 78.2 | — | 69 | — |

TABLE 7-continued

Chloride (C) Concentrations in Methane Cometabolism Test Plot
(reported in mg/L)

| Sample ID | 30 | 44 | 58 | 85 | 143 | 224 (before/after purging) |
|---|---|---|---|---|---|---|
| METHMP-4 | 58.2 | 54.9 | 101.6 | 76.6 | 20 | — |
| METH-MW | — | 25.6 | — | — | 38 | — |

TABLE 8

Tentatively Identified Compounds (TIC) in Confirmatory Soil Samples
Summary of Laboratory Results Using EPA Method 8270

| Compound Name | CAS Number | Average Retention Time (min) | Estimated Concentration (mg/kg) Sample ID | | | | |
|---|---|---|---|---|---|---|---|
| | | | 1 | 2 | 3 | 4 | 5 |
| 2-Pentanone, 4-hydroxy-4-methyl- | 123-42-2 | 2.655 | 9.6 | 8.7 | 11 | 11 | 0 |
| Tricyclo {2.2.1.$\phi^{2,6}$}heptane, 1,7,7-trimethyl- | 508-32-7 | 3.245 | 0 | 0 | 10 | 0 | 21 |
| Bicyclo[3.1.1]hept-2-ene, 2,6,6-trimethyl- | 80-56-8 | 3.334 | 16 | 16 | 33 | 0 | 26 |
| 1,3,6-Heptatriene, 2,5,5-trimethyl- | 29548-02-5 | 3.447 | 0 | 0 | 59 | 0 | 69 |
| Benzene, 1-chloro-2-methyl- | 95-49-8 | 3.464 | 38 | 35 | 0 | 0 | 0 |
| Benzene, 1-chloro-4-methyl- | 106-43-4 | 3.491 | 36 | 19 | 18 | 0 | 21 |
| Benzene, 1-ethyl-2-methyl- | 611-14-3 | 3.511 | 0 | 0 | 0 | 11 | 0 |
| Benzene, 1,3,5-trimethyl- | 108-67-8 | 3.559 | 0 | 0 | 0 | 4.1 | 0 |
| Cyclohexane, 3-methyl-6-(1-methylethyl)-, trans | 1124-26-1 | 3.786 | 0 | 0 | 13 | 0 | 0 |
| 1,3-Cyclohexadiene, 2-methyl-5-(1-methylethyl)- | 99-83-2 | 3.821 | 0 | 0 | 9.4 | 0 | 0 |
| 1,3-Cyclohexadiene, 1-methyl-4-(1-methylethyl)- | 99-86-5 | 3.916 | 0 | 0 | 26 | 0 | 0 |
| 1-Hexanol, 2-ethyl- | 104-76-7 | 3.937 | 26 | 32 | 0 | 0 | 32 |
| Benzene, 1-methyl-4-(1-methylethyl)- | 99-87-6 | 3.987 | 0 | 0 | 180 | 0 | 0 |
| Phenol, 2-methyl- | 95-48-7 | 4.104 | 0 | 6.8 | 0 | 0 | 0 |
| Benzene, 1,2-dichloro-3-methyl- | 32768-54-0 | 4.650 | 120 | 76 | 190 | 110 | 68 |
| Benzene, 1,2-dichloro-4-methyl- | 95-75-0 | 4.803 | 0 | 0 | 0 | 0 | 71 |
| Benzene, 1,3-dichloro-2-methyl- | 118-69-4 | 4.851 | 0 | 0 | 0 | 130 | 0 |
| Benzene, 1,2,4-trichloro-3-methyl- | 2077-46-5 | 5.613 | 16 | 0 | 9.8 | 5.4 | 0 |
| Benzene, 1,2,3,5-tetrachloro- | 634-90-2 | 6.213 | 0 | 0 | 0 | 0 | 32 |
| Benzene methanol, 2,4-dichloro- | 1777-82-8 | 6.346 | 0 | 0 | 16 | 0 | 0 |
| Benzene, 1,1'-(1,2-ethenediyl) bis- | 103-29-7 | 6.960 | 0 | 10 | 0 | 0 | 0 |
| Benzene, 1-methyl-2-(phenylmethyl)- | 713-36-0 | 7.010 | 0 | 15 | 0 | 0 | 15 |
| Benzene, 1-methyl-4-(phenylmethyl)- | 620-83-7 | 7.037 | 0 | 16 | 0 | 0 | 12 |

What is claimed is:

1. A method of remediating methanotrophic bacteria-containing soil contaminated with organochlorine pesticides selected from the group consisting of toxaphene dieldrin, lindane, aldrin, chlordane, endrin endrin aldehyde heptachlor, heptachlor epoxide, alpha-BHC, beta-BHC, gamma-BHC, delta-BHC, 4,4$^1$-DDD, 4,4$^1$-DDE, 4,4$^1$-DDT, endosulfan I, endosulfan II, and endosulfan sulfate, comprising introducing an effective concentration of a gaseous methane/air mixture containing about 1% to about 8% methane in the mixture to the soil and degrading said pesticides by aerobic methane co-metabolism.

2. A method of remediating methanotrophic bacteria-free soil contaminated with organochlorine pesticides selected from the group consisting of toxaphene, dieldrin, lindane, aldrin, chlordane, endrin, endrin aldehyde heptachlor, heptachlor epoxide, alpha-BHC, beta-BHC, gamma-BHC, delta-BHC, 4,4$^1$-DDD, 4,4$^1$-DDE, 4,4$^1$-DDT, endosulfan I, endosulfan II, and endosulfan sulfate, comprising the steps of:

(a) introducing methanotrophic bacteria to the soil; and
(b) introducing an effective concentration of a gaseous methane/air mixture containing about 1% to about 8% methane in the mixture to the methanotrophic bacteria- -containing soil and degrading said pesticides by aerobic methane cometabolism.

3. The method of claim 1 wherein the organochlorine pesticide is toxaphene.

4. The method of claim 1 wherein the concentration of methane in air is in the range of from about 2% to about 5%.

5. The method of claim 2 wherein the organochlorine pesticide is toxaphene.

6. The method of claim 2 wherein the concentration of methane in air is in the range of from about 2% to about 5%.

* * * * *

UNITED STATES PATENT AND TRADEMARK OFFICE
CERTIFICATE OF CORRECTION

PATENT NO.: 5,908,774

DATED: June 1, 1999

INVENTOR(S): Edward A. Shaw

It is certified that errors appear in the above-identified patent, and that said Letters Patent is hereby corrected as shown below.

Column 11, Claim 1, line 58, after "toxaphene" insert --,--

Column 11, Claim 1, line 59, after "chlordane, endrin" insert --,--

Column 13, Claim 2, line 2, delete "cometabolism" and insert --co-metabolism--

Signed and Sealed this

Fifth Day of October, 1999

Attest:

Q. TODD DICKINSON

Attesting Officer

Acting Commissioner of Patents and Trademarks